(12) United States Patent
Haraldsson et al.

(10) Patent No.: US 6,585,682 B1
(45) Date of Patent: Jul. 1, 2003

(54) METHOD AND APPARATUS FOR PREVENTING PROTEIN LOSS WITH PERITONEAL DIALYSIS

(75) Inventors: Börje Haraldsson, Landvetter (SE); Jan-Bertil Jeppsson, Lomma (SE); Bengt-Olov Thell, Fyinge (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/856,287

(22) PCT Filed: Nov. 19, 1999

(86) PCT No.: PCT/SE99/02143
§ 371 (c)(1),
(2), (4) Date: Jul. 5, 2001

(87) PCT Pub. No.: WO00/30701
PCT Pub. Date: Jun. 2, 2000

(30) Foreign Application Priority Data

Nov. 20, 1998 (SE) ................................................ 9803987

(51) Int. Cl.[7] .............................................. A61M 1/00
(52) U.S. Cl. .......................................... 604/29; 604/28
(58) Field of Search ........................ 604/29, 4.01, 5.01, 604/5.04, 6.09, 6.11, 6.13, 93.01, 113, 131, 151, 264, 272, 523; 210/644, 645, 646, 649, 650, 651, 757, 175, 181, 194, 195.2, 348, 439, 500.1

(56) References Cited

U.S. PATENT DOCUMENTS

| 4,276,175 A | 6/1981 | Bower ........................ 210/636 |
| 4,338,190 A | 7/1982 | Kraus et al. .............. 210/195.2 |
| 4,618,343 A | * 10/1986 | Polaschegg .................. 604/29 |
| 5,141,493 A | 8/1992 | Jacobsen et al. ............... 604/29 |
| 5,643,201 A | * 7/1997 | Peabody et al. ............... 604/31 |

FOREIGN PATENT DOCUMENTS

| EP | 0 928 615 A1 | 7/1999 |
| WO | 97/4733 | 12/1997 |

* cited by examiner

Primary Examiner—Manuel Mendez
Assistant Examiner—Mark K Han
(74) Attorney, Agent, or Firm—Lerner, David, Littenberg, Krumholz & Mentlik, LLP

(57) ABSTRACT

Methods of peritoneal dialysis are disclosed including draining spent peritoneal dialysis solution from a patient to a drain bag, passing the spent peritoneal dialysis solution from the drain bag through a filter so as to separate a protein rich fraction and a protein lean fraction therefrom, and supplying the protein enriched fraction to the fresh peritoneal dialysis solution for supply to the patient. Apparatus for peritoneal dialysis is also disclosed.

10 Claims, 8 Drawing Sheets

METHOD AND APPARATUS FOR PREVENTING PROTEIN LOSS WITH PERITONEAL DIALYSIS

FIELD OF THE INVENTION

The invention relates to the field of peritoneal dialysis, so-called PD, and in particular to automatic peritoneal dialysis, so-called APD. A problem with peritoneal dialysis is loss of protein, particularly albumin. More particularly, the invention relates to a method and an apparatus for preventing protein loss with PD.

BACKGROUND ART

Peritoneal dialysis means that dialysis occurs by using one of the body's own membranes in the peritoneal cavity, the peritoneal membrane. A PD solution is placed in the peritoneal cavity inside the peritoneal membrane by means of a catheter which passes through the skin and into the peritoneal cavity. Slightly more than two liters of fluid can often be placed in the peritoneal cavity without the patient feeling any great discomfort.

The most common form of PD today is CAPD, continuous ambulatory peritoneal dialysis. With CAPD, a set of bags is used which are coupled to the patient's catheter, in order, with the aid of gravity, to drain the spent PD solution from the patient's peritoneal cavity into a waste bag and to add new PD solution to the patient from a sterile storage bag.

With APD, a machine is used, a so-called cycler, for achieving the necessary flows into and out of the patient. The machine transports PD solution from storage bags to the cycler, where it is heated, and further to the patient, and transports the PD solution from the patient to the cycler and further to a waste receiver. The cycler is provided with a measurement device which monitors the flows into and out of the patient. APD can be used during the night and may be more effective than CAPD. With APD, the patient avoids heavy lifting since the PD solutions do not need to be hung up in a high position which is required with CAPD.

One complication with dialysis is protein loss. The patient often has a low amount of protein in the blood already long before the treatment starts. The dialysis treatment brings about additional losses of protein. A low protein content in a patient is a risk factor which is coupled to high morbidity and mortality with hemodialysis.

In a normal healthy patient, the peritoneal cavity contains about 200 ml of a solution with a composition which is similar to blood plasma. This liquid contains proteins such as albumin and immunoglobins in a predetermined concentration. The concentration of albumin (20–30 g/l)in the peritoneal cavity is made up of an inward flow from the blood path to the peritoneal cavity, which normally occurs through the peritoneal membrane, and an outflow of albumin via the lymph pathways. The composition of the fluid varies from person to person.

With peritoneal dialysis, the protein content in the fluid inside the peritoneal cavity is diluted and its colloid osmotic pressure is thereby lowered, that pressure being however replaced by a high glucose amount which creates the necessary crystal osmotic gradient in order to remove fluid from the patient.

The fluid which is present in the peritoneal cavity during peritoneal dialysis is thus different than that which is normally present in the peritoneal cavity of healthy persons in at least two respects, namely a high glucose content and a low protein content. There is reason to believe that both characteristics may lead to complications and it would be desirable to raise the content of protein in order thereby to be able to reduce the glucose content.

It is known that the increased exposure to glucose in a PD patient may lead to hyperinsulinemia with associated risk of cardio-vascular disease.

Additionally, a daily loss of albumin and other protein substances of about 5 g–25 g occurs by the spent dialysis solution being led to a waste receiver or to a waste bag which is later discarded.

The abnormally low content of immunoglobulins which are present in the peritoneal cavity during PD probably contributes to increased risk of peritonitis.

Protein has a buffer capacity, and a reduced content of proteins in the peritoneal cavity means that a PD solution with low pH is neutralised to a lesser extent, or more slowly, during the fill of the peritoneal cavity.

With PD it has previously been proposed to circulate the PD solution in a closed circuit, whereby protein losses and losses of other substances are avoided. The PD solution is allowed to pass on one side of a membrane in a dialyser where the PD solution is regenerated by dialysis against an outer dialysis solution whereby waste products are removed, see U.S. Pat. Nos. 4,338,190, 5,141,493 and 4,276,175.

In WO 97/47337, the D solution is regenerated by means of a semi-permeable membrane in order to raise the osmotic effect of the proteins within the PD solution and to use these proteins as osmotic means. If necessary, other components such as electrolytes or amino acids are added.

These known constructions attack the problem of protein loss. However these known constructions are difficult to carry out in practice.

They require use of a double-lumen-catheter with simultaneous inlet and outlet to the peritoneal cavity, in order to obtain a continuous flow. It can be difficult to make such a continuous flow be effective since it easily happens that the PD solution passes more or less straight through between the inlet and the outlet without coming into close contact with the peritoneal membrane.

Another problem is that a circulation pump is required in order to drive the PD solution in the intended circuits. The pump has to have the capacity to achieve the required circulation. If any component in the circuit should have a fault, such as a hole in a semi-permeable membrane, there is a risk that the patient will be subjected to much too large a pressure from the pump, being either an under-pressure or an over-pressure.

A third problem is that the aforementioned constructions are often expensive since they need many and expensive components, both in the required cycler and for disposable components.

SUMMARY OF THE INVENTION

A first object of the present invention is to achieve a method and an apparatus which prevents protein loss with peritoneal dialysis, particularly with APD.

A second object of the invention is to achieve a method which is such that it can be used with a conventional cycler, whereby the cost can be kept low.

A third object of the invention is to achieve a method and an apparatus which do not risk subjecting the patient to too high a pressure even if a fault should occur in the disposable products which are used.

A fourth object of the invention is to achieve a method and an apparatus which can be used with a normal catheter having only one passage.

A fifth object of the invention is to achieve a method and an apparatus which prevents protein loss and in which dialysis solution is continuously or intermittently supplied from a source of PD solution and spent PD solution is continuously or intermittently removed from the patient to a waste receiver.

In order to meet these objects, a method is provided according to the invention for preventing protein loss with peritoneal dialysis, comprising draining spent PD solution from a patient to a drain bag, passing the spent PD solution in the drain bag through a filter device for enrichment of a protein-rich fraction, and supplying the protein-rich fraction to a fresh PD solution intended to be supplied to the patient.

The protein-rich fraction or filter retentate is suitably collected in a protein bag for later supply to the fresh PD solution, whilst the protein-lean fraction or filtrate passing through the filter is sent to a waste receiver.

The protein bag may be positioned at a predetermined height above the filter in order to achieve a hydraulic back-pressure.

The invention also relates to an apparatus for carrying out the aforementioned method. The apparatus includes a device for draining spent PD solution from a patient to a drain bag, a device for passing spent PD solution in the drain bag through a filter device for enrichment of a protein-rich fraction, and a device for supplying the protein-rich fraction to a fresh PD solution intended to be supplied to the patient.

The apparatus also suitably comprises a device for collecting the protein-rich fraction in a protein bag for later supply to the fresh PD solution, and a device for sending the protein-lean fraction passing through the filter to a waste receiver.

BRIEF DESCRIPTION OF THE DRAWINGS

Additional objects, advantages and features of the invention are disclosed in more detail in the following detailed description of several embodiments of the invention with reference to the drawings.

DETAILED DESCRIPTION OF EMBODIMENTS

Figure 1:
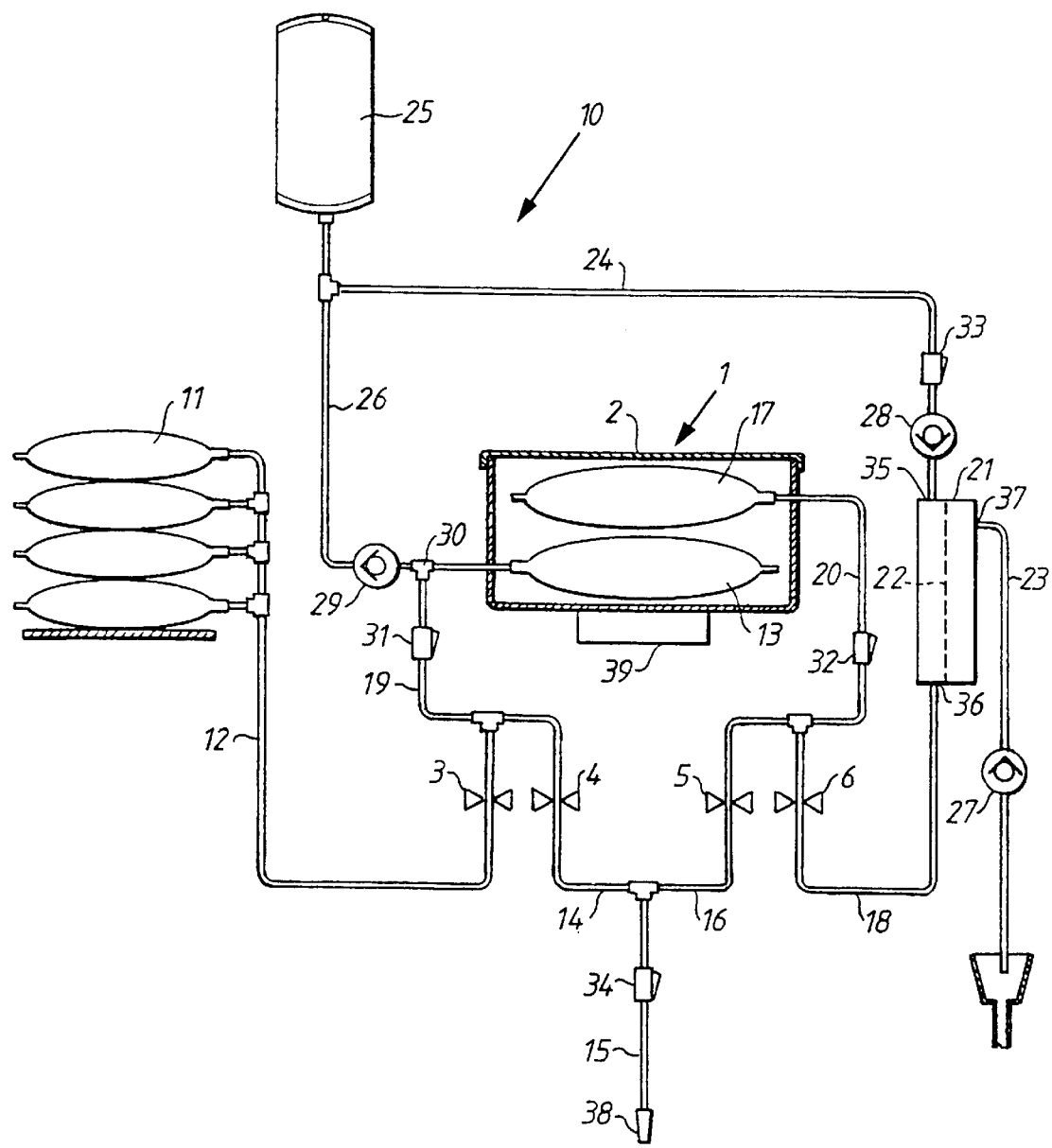
FIG. 1 is a schematic diagram of the principle of a cycler provided with a tube-set intended for APD and where the present invention can be used, in an initial position.

FIG. 1 discloses an overview of a cycler and a tube-set intended for APD and during use of the present invention.

The cycler is shown very schematically and only consisting of a pressure chamber 2 and four valve clamps 3, 4, 5, 6. The cycler is of a construction which is disclosed in WO 95/20985, to which reference is made for further details. WO 95/20985 is incorporated in the present application by reference.

The cycler is provided with a tube-set 10. Consisting of several bags joined together with tubes. The tube-set can be manufactured of PVC and is sterilised. More closely defined, the tube-set includes storage bags 11 for fresh PD solution, FIG. 1 showing four bags coupled in parallel. The storage bags 11 are joined by first tube 12 to a heater bag 13. The heater bag 13 is furthermore joined with a patient via a second tube 14 and a patient connector tube 15. The patient connector tube 15 is joined via a third tube 16 to a drain bag 17 which, in turn, is joined to a waste receiver via a fourth tube 18.

The heater bag 13 and the drain bag 17 are positioned in the pressure chamber 2. The tubes 12, 14, 16, 18 pass through valve clamps as shown in FIG. 1. The tubes 12 and 14 unite into a common tube 19 beyond the valve clamps, which tube 19 leads via a through-way bushing into the pressure chamber to the heater bag 13. In a similar way, the tubes 16 and 18 unite beyond the valve clamps 5, 6 into a common tube 20 which leads via a through-way bushing into the pressure chamber to the drain bag 17.

As is clear from WO 95/20985, the pressure chamber 2 can be subjected to an under-pressure or an over-pressure. The pressure chamber can, together with the valve clamps 3, 4, 5 and 6, control the flow of fresh PD solution from the storage bags to the heater bag, and from there to the patient, and spent PD solution from the patient to the drain bag and further to the waste receiver. The flow is monitored in that the pressure chamber is weighed on electronic scales, whereby the flow of PD solution into and out of the heater bag and drain bag, respectively, can be detected and controlled.

Different PD operation cycles are possible, which is understood by a skilled man and which is described in more detail in WO 95/20985.

In order to prevent protein loss in accordance with the present invention, the previously known tube set is somewhat modified. Thus, a filter 21 with a semipermeable membrane 22 is added to the tube 18 which leads to the waste receiver. The semipermeable membrane has a structure and dimensions such that it holds or prevents passage of molecules and particles larger than a minimum diameter, which is normally defined in terms of molecular weight for the molecules which cannot pass through the membrane. In the present case, the semipermeable membrane has the capacity to hold molecules larger than about 20 000 to 50 000 Daltons. The membrane is constructed so as to safely prevent passage of albumin which has a molecular size of 68 000 Daltons. The protein-lean fraction which passes through the membrane is led via a fifth tube 23 to the waste receiver.

The protein-rich fraction which cannot pass through the membrane is led via a sixth tube 24 to a protein bag 25. A seventh tube 26 leads from the protein bag 25 to a T-coupling 30 on the tube 19, which leads to the heater bag 13.

Additionally, the tube set is provided with three one-way valves 27, 28 and 29 in tubes 23, 24 and 26, respectively, as shown in FIG. 1. Furthermore, there are three tube clamps 31, 32 and 33 arranged on the tubes 19, 20 and 24 respectively, as shown in FIG. 1.

The function of the invention will be disclosed in the following description by the various steps in the method according to the invention with reference to FIGS. 2–6.

Before the invention can be applied, the filter needs to be "primed", i.e. filled with fluid so that all the air within the filter is displaced. This occurs in a first priming step which is described with reference to FIG. 1. Firstly the clamps 31, 32 and 33 are closed as well as a clamp 34 located on the patient tube. The filter 22 is adjusted such that the end positioned closest to the connection 37 to the tube 23 is highest. The valves 3, 4, 5 and 6 are opened, which may occur manually or in another suitable way. One of the storage bags 11 is raised up somewhat so that it is located above the level of the filter, whereby the PD solution flows through the tube 12, the valve 3 and the valve 4 to the tube 14 as well as further via the tube 16 and the valves 5 and 6 to the tube 18 where the PD solution reaches the lower connection 36 of the filter. In this way the PD solution forces the air which is in the filter out through the connection 37 and via the tube 23 to the waste receiver. Since the clamps 31, 34, 32 and 33 are closed, no solution will flow into the heater bag 13, the patient connection tube 15, the drain bag 17 or the tube 24. When the filter is completely full with PD solution and there are no more air bubbles in the tube 23, the tubes clamp 34 is opened so that the patient connection 15 is also filled with PD solution up to the patient connector 38, whereupon the clamp 34 is closed again.

It is understood that as an alternative to using PD solution for priming purposes, a separate bag with priming solution such as a sterile physiological common salt solution can be connected to a coupling on the tube 12.

Parts of the tube set and the filter are now filled with PD solution. Then the tube clamps 31, 32 and 33 are removed and the cycler is ready for use.

Figure 2:
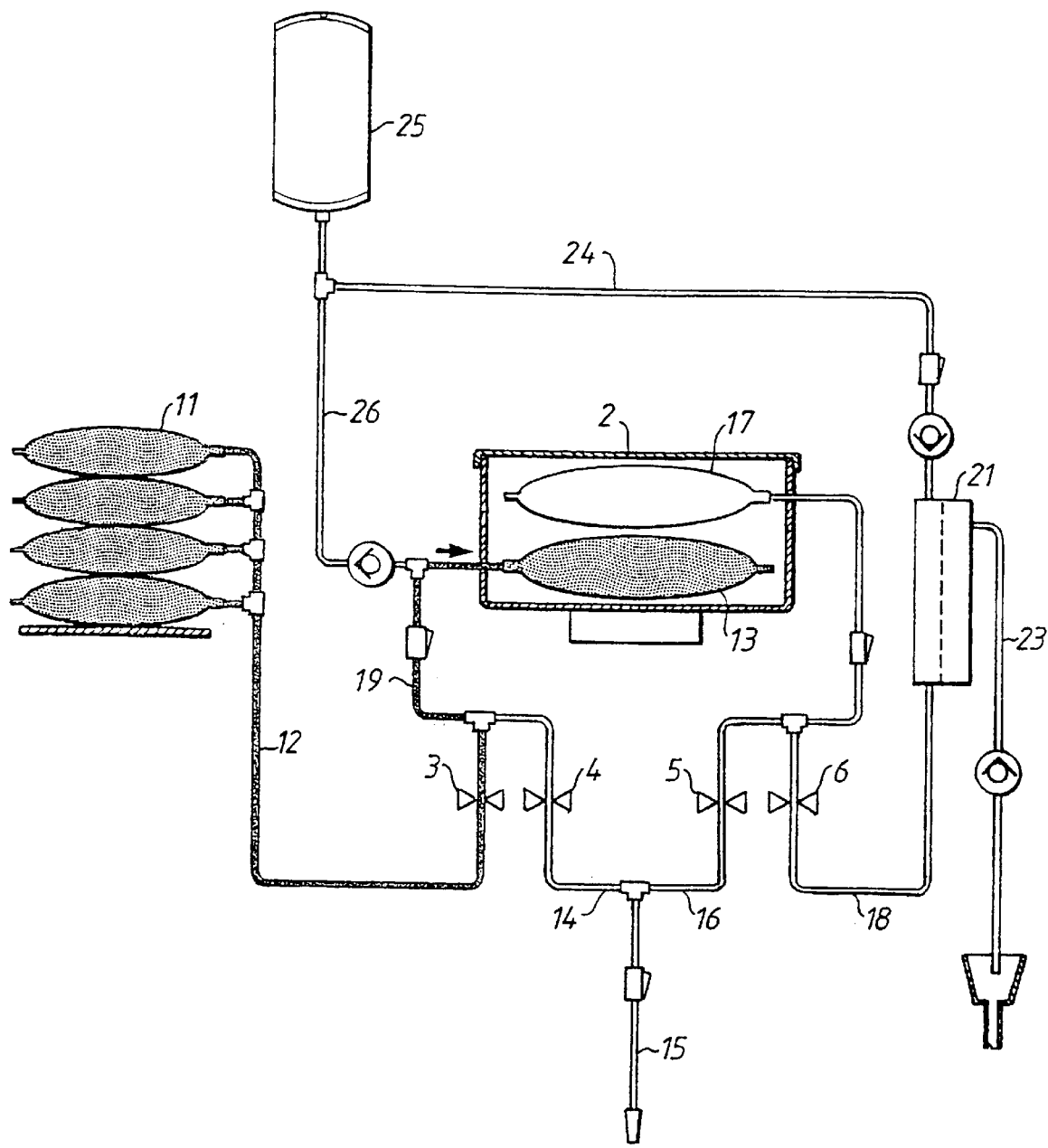
FIG. 2 is a schematic diagram of the principle of the cycler in FIG. 1 in a first position, called HF.

As is clear from FIG. 2, the cycler proceeds by filling the heater bag with PD solution from the storage bags 11 (Heater Fill, HF) by the valve 3 being opened when the pressure chamber has an under-pressure (−100 mm Hg). The other valves are closed. The contents in the heater bag is heated to about 37° C. The amount of PD solution which is fed into the heater bag is determined by the user by entering a patient fill volume into the cycler's computer 39 and is regulated with the aid of the cycler's scales.

During this time, the patient connects himself to the patient coupling 38 using aseptic technology in a conventional way. Thereafter, the clamp 34 is opened or removed. The tubes 14 and 16 are suitably united into a double tube so that the tube 15 is as short as possible, which minimises the dead space (see EP 499 718).

Thereafter, the patient is emptied of spent PD solution (Patient Drain, PD) which occurs by the pressure chamber being exposed to an under-pressure of about −65 mm Hg and the valve 5 is opened whilst the other valves are shut. The spent PD solution flows from the patient via the tubes 15, 16 and 20 to the drain bag 17. When the drain step is complete, the valve 5 is shut, which is determined by the flow to the drain bag having stopped or having been reduced in a predetermined way.

Then, the cycler carries out steps which are particularly related to the present invention. This occurs during a system drain step (System Drain, SD) shown in FIG. 4, where the contents in the drain bag is fed out to the waste receiver. The pressure chamber is exposed to an over-pressure of about +100 mm Hg and the valve 6 is opened whilst the other valves are closed. In this way the contents in the drain bag 17 is fed out via the tubes 20 and 18 to the inlet connector 36 of the filter.

The protein bag 25 is arranged on a stand at a predetermined height above the cycler 1 and the filter 21. The PD solution which enters the filter via the connector 36 first passes straight through the filter and out through the outlet 35 to the tube 24 until the hydrostatic pressure causes a part of the fluid in the PD solution to be passed through the filter and out to the outlet via the tube 23. The retentate fraction which is held by the filter is thereby enriched in protein and other substances having a molecular weight over about 50 000 Daltons. The enriched fraction on the inlet side of the membrane applies a colloidosmotic pressure across the membrane. When the mentioned osmotic pressure is equal to the hydrostatic back-pressure in the tube 24, the retentate fraction cannot be further enriched and is passed to the protein bag 25.

By adjusting the height of the protein bag and depending upon the characteristics of the filter, a part of the contents in the drain bag will be filtered and pass out to the waste receiver via the tube 23, the filtrate, and a part will pass to the protein bag, the retentate. The volume ratio between the protein-rich fraction and the protein-lean fraction can be about 5–25% depending on the height of the protein bag and the amount of protein in the contents of the drain bag. The higher the protein content in the drain bag, the higher its osmotic effect and the lower the proportion of the volume passing to the waste receiver.

In accordance with the invention it is sought to concentrate the protein-rich fraction as much as possible without the fraction becoming too viscous or having too high an osmotic pressure arising across the membrane. A degree of concentration of 4 to 20 is sought.

When the drain bag is emptied and all the spent PD solution has either been fed out to the waste receiver via the filter or has been moved to the protein bag, this step is finished which is controlled with the aid of the scales in the cycler.

Then, all the valves 3–6 are closed while the pressure in the pressure chamber drops from +100 mm Hg to −65 mm Hg. Then, the contents in the protein bag can flow via the tube 26 to the heater bag in a protein filling step (Protein Fill, PrF). The one-way valve 28 ensures that the protein fraction does not flow back to the filter 21. The heater bag 13 is already filled with PD solution so the protein fraction is diluted to about the same or slightly lower concentration as it originally had in the drain bag.

By transfer of the protein fraction, the contents of the heater bag will increase, but the increase is mediocre and is tolerated in most cases by the patient. In other cases the fill volume may be slightly reduced. The increase in the volume is monitored by the machine via its scales.

Lastly a patient fill (Patient Fill, PF) occurs by the pressure chamber being exposed to an over-pressure of about +80 mm Hg and the valve 4 is opened whilst the other valves are shut.

After this, the sequence is resumed by a filling of the heater bag (HF).

By using the filter 21 and the protein bag 25 the proteins which are in the used PD solution will be utilised and fed back to the patient via the contents in the heater bag. The protein fraction in the drain bag is concentrated as much as possible before it is transferred to the heater bag, since the fluid which follows with the protein fraction becomes ineffective with respect to the dialysis treatment since it has already been used once.

In this way, the protein content in the patient's peritoneal cavity will adjust itself to a value where the inflow via the peritoneal membrane balances the outflow via the lymph pathways, as in a healthy patient, but the volume of fluid in the peritoneal cavity is about 10 times larger. In this way the osmotic effect of the proteins will be utilised, which can be used to reduce the concentration of glucose in the PD solution.

Reduced glucose load is expected to give reduced hyperinsulinemia, which reduces the risk for arteriosclerosis and thereby reduces complications in the form of cardiovascular complications.

It can be expected that the higher protein content in the PD solution will have a beneficial effect on the peritoneal membrane so that its characteristics vary less during the dialysis treatment. Additionally, the increased concentration of immunoglobulins may result in a reduced occurrence of peritonitis.

The supply of the protein fraction to the contents in the heater bag means a neutralisation of the contents so that it obtains a physiological pH of about 7.2–7.4. In this way an exposure of the peritoneal cavity to a solution with too low a pH is avoided, which exposure is understood to cause pain during the fill phase and may result in damage to the peritoneal membrane and the cells which are in the peritoneal cavity.

Additionally the proteins absorb the glucose degradation products which are in the contents of the heater bag, so that these products are not able to act on the proteins and other amino compositions which are present in the peritoneal cavity. These glucose degradation products are presumed to be AGE precursors. Thus, the exposure of the patient to AGE-inducing substances is thus decreased.

The extra steps which are required according to the invention increase the time from the patient drain (PD) to the patient fill (PF), thereby reducing the effective dialysis time. Without using the invention, a patient drain should be able to be followed directly by a patient fill without an intermediate system drain and protein bag filling. The time span between these two steps may be about 10 minutes. However the beneficial effects of the invention should outweigh this disadvantage.

Figure 3:
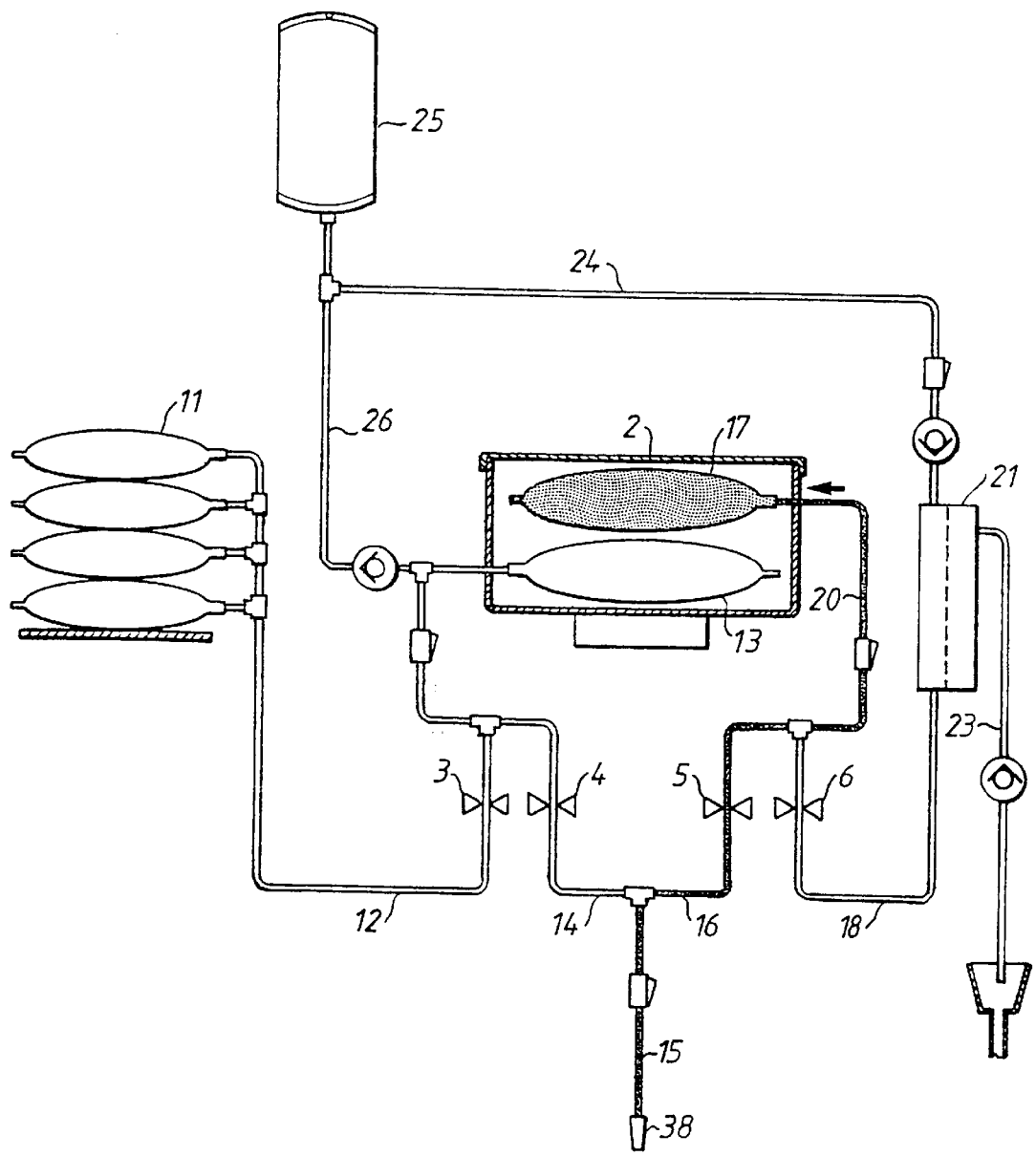
FIG. 3 is a schematic diagram of the principle of the cycler in FIG. 1 in a second position, called PD.
Figure 4:
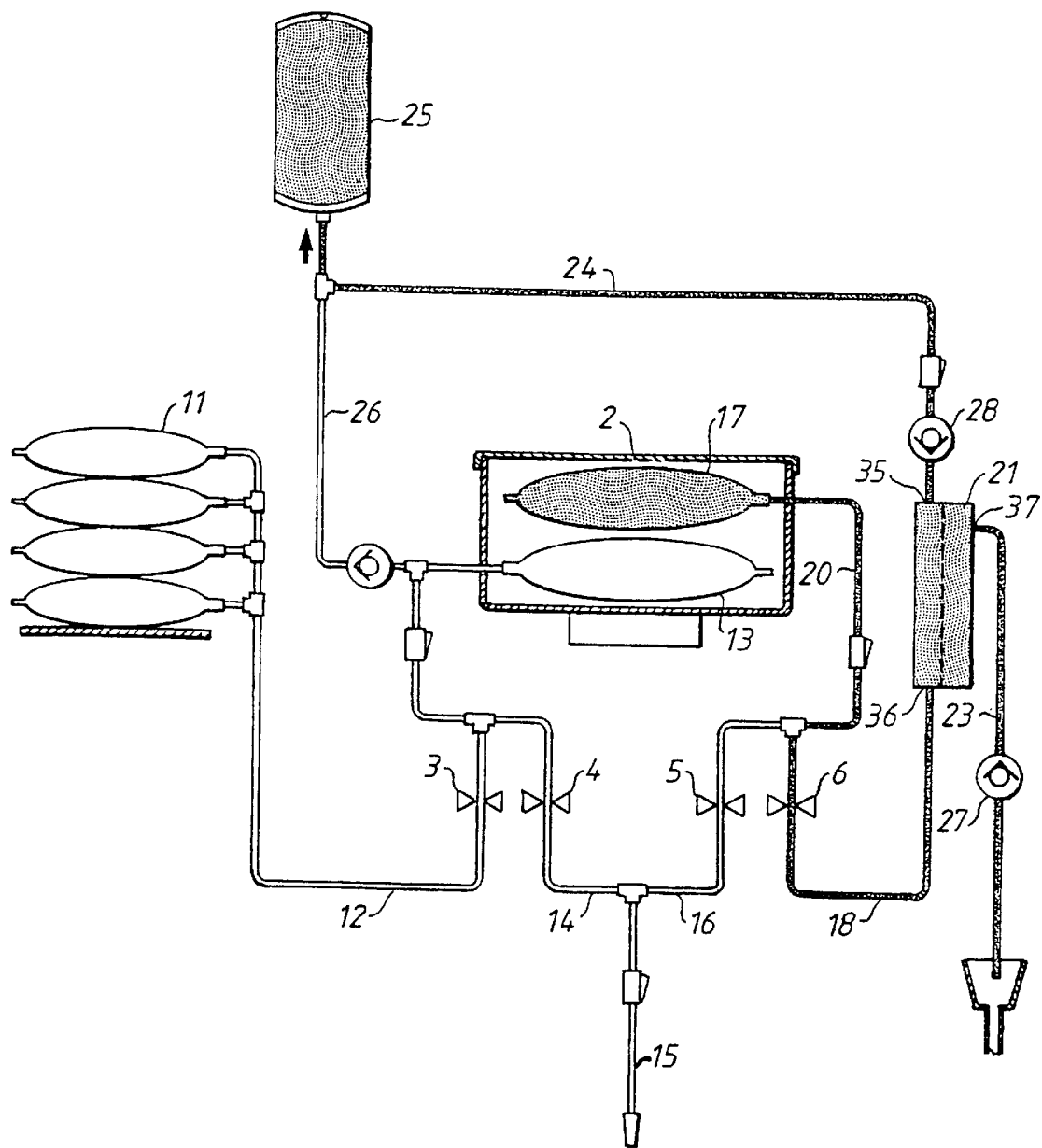
FIG. 4 is a schematic diagram of the principle of the cycler in FIG. 1 in a third position, called SD.
Figure 6:
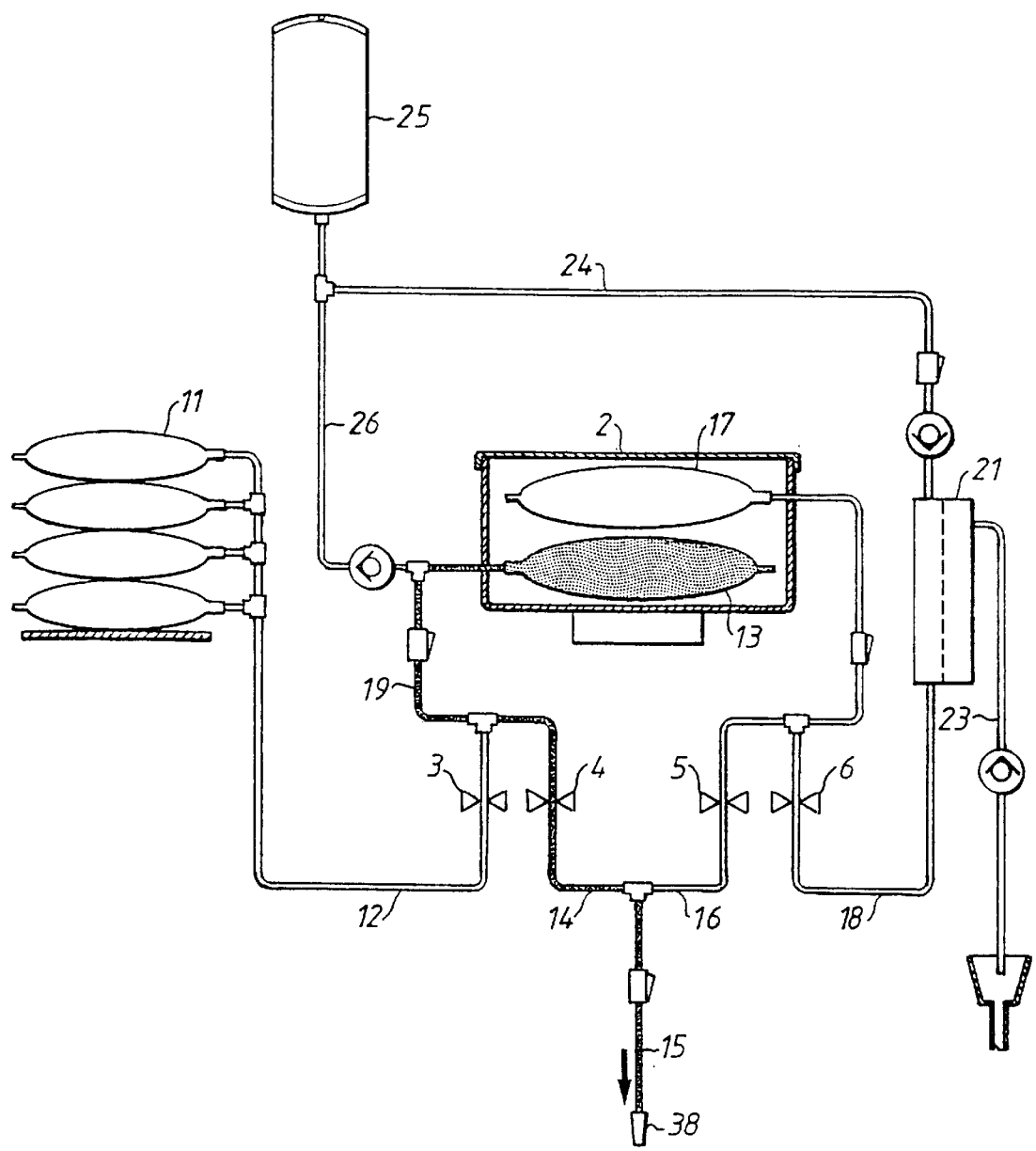
FIG. 6 is a schematic diagram of the principle of the cycler in FIG. 1 in a fifth position, called PF.

It is possible to carry out the separation of the contents of the drain bag after the patient fill, i.e. the step in FIG. 6 is placed between the steps according to FIG. 3 and 4. In this way, no dialysis treatment time is lost. The protein bag will then contain the protein-rich fraction between the patient fills and feed this directly into the heater bag before the patient fill. However, the first patient fill will occur with a contents in the heater bag which is not enriched with proteins. The next patient fill will however occur with an acceptably high protein concentration.

The last patient fill during the night should however occur in the way described first, so that the PD solution fed out from the patient is first separated for protein and this protein fraction is supplied to the patient in addition to the fraction which has already been supplied, i.e. a full dose of protein is supplied to the patient. In this way, the proteins are always stored in the patient's peritoneal cavity between dialysis treatments, such as during the daytime for a patient being treated with APD during nighttime.

Alternatively the last protein dose can also be stored in the protein bag during the day and at the start of the next treatment this protein dose can also be used to protein-enrich the first patient fill. This requires however that the protein fraction is not damaged by being stored during the day up to the connection of the patient the next evening and that bacteria have no possibility to grow.

Normally, the heater bag includes about 10%–15% extra PD fluid, which is not filled to the patient, because of the risk of entering air into the patient. Such air is always present in the system and is separated from the fluid in the heater bag during the heating step and accumulates in the heater bag. By infusing less than the complete contents of the heater bag, such air remains in the top of the heater bag. The remaining 10% in the heater bag is discarded after a completed peritoneal dialysis session, such as a night APD treatment. However, this also means that 10% of the albumin present in the last fill to the patient is wasted. Since the concentration is relatively high, such as 20 g/l, this means that up to 4–6 gram albumin is wasted for a two liter fill volume.

According to the invention, this waste of albumin may be avoided by making a separate and different last fill step. Normally, the last fill is anyhow different, since the patient in the last fill is prepared for the day time dwell, which may be with a different composition or concentration of glucose, or with a glucose polymer instead of glucose.

Figure 5:
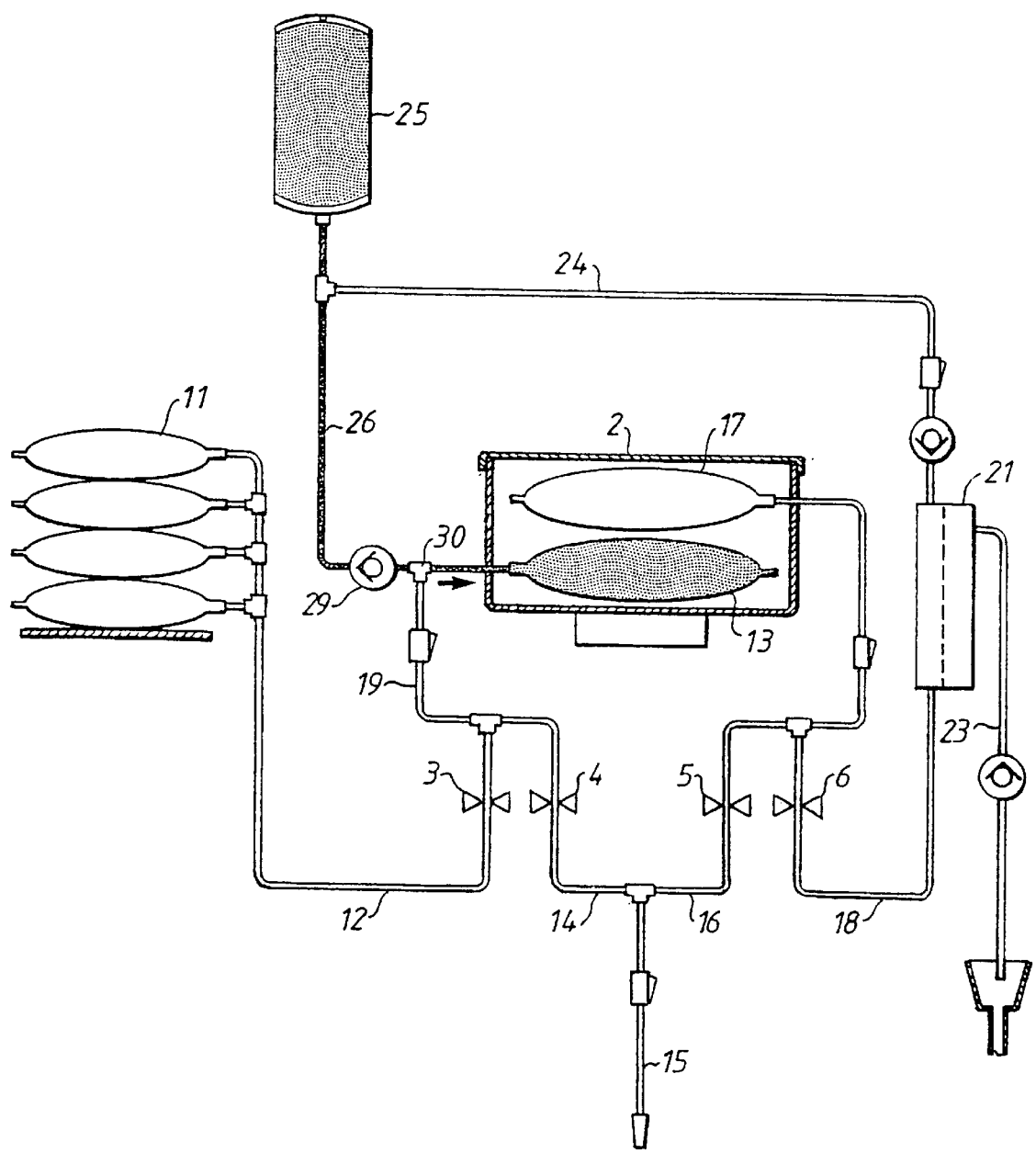
FIG. 5 is a schematic diagram of the principle of the cycler in FIG. 1 in a fourth position, called PrF.

Instead of entering the contents of the protein bag into the heater bag, the concents of the protein bag is delivered directly to the peritoneal cavity in advance of the last fill. In order to perform this operation, the tube set shown in FIG. 5 is sligtly modified by moving clamp 31 in FIG. 5 to a position between T-connection 30 and heater bag 13, in the position shown in FIG. 9 by reference numeral 31*b*. Another clamp 31*a* is inserted in tube 12 and another clamp 33*a* is inserted in tube 23.

Instead of entering the contents of the protein bag 25 into the heater bag in the last fill, clamp 31*b* is closed while valve clamp 4 is opened. Due to the gravity forces, the contents of protein bag flows down the tubes 26, 19, 14 and 15 into the patient's peritoneal cavity, which at this time is essentially empty. When all the contents of the protein bag has been filled into the patient, clamp 31*b* is opened and the contents of heater bag is filled to the patient. In this manner, only about 1% (about 0,4 grams per day) of the protein is wasted, namely the protein remaining in the heater bag after the second last fill, and diluted by about two liters of fresh PD solution, of which about 90% is filled to the patient in the last fill.

There is also a waste of protein because some protein are left in the filter and the tube 24. In order to save also these proteins, a separate scavenging step is performed, either before or immediately after the above-mentioned direct protein fill step. Clamp 31*a* in tube 12 and clamp 33*a* in tube 23 are closed. Moreover, clamp 34 in tube 15 and clamp 32 in tube 20 are closed. Clamp 31*b* in tube 19 as well as all valve clamps 3, 4, 5 and 6 are opened. The pressure chamber is exposed to an over-pressure, whereby the fluid in the heater bag passes through tube 19, tube 14, tube 16 and tube 18 to the filter 21. Because clamp 33*a* in tube 23 is closed, the fluid passes up through tube 24, clamp 33 being opened, to protein bag 25, thereby bringing all proteins stuck in the retentate side of filter 21 and tube 24 to the protein bag. When about two deciliters have passed this path, as measured by the scales of the cycler, the scavening step is finnished by closing all valve clamps 3, 4, 5 and 6 and opening clamp 34. Finally, the contents of the protein bag is entered to the peritoneal cavity of the patient. If the scavening step is performed before the protein patient fill step, the proteins saved by the scavenging step is introduced into the patient together with the other proteins. Otherwise, valve 4 is opened with clamp 31*b* closed and clamp 34 opened, and the contents of the protein bag is entered into the peritoneal cavity of the patient. Finally, the contents of the heater bag is filled to the patient as explained above. These three steps may be performed in any desired order.

The method of direct fill of the protein bag to the patient may be performed automatically by using autmoatically controlled valve clamps in the circuit instead of the manually operated clamps. The method of direct fill of the protein bag to the patient may also be used in more than the last fill, such as also in the second last fill, etc.

The method according to the invention is beneficial relative to other previously suggested methods for regeneration of the PD solution, since the spent PD solution is filtered, not dialysed. Such molecules as beta-2-microglobulin which are presumed to cause complications, pass through the filter and to the waste receiver. Also other so-called "middle molecules" pass through the filter since these follow with the ultrafiltration flow. In previously known methods, dialysis is used to regenerate the PD solution and it is known that dialysis is not equally as effective as filtration in eliminating these "middle molecules".

By means of the invention, a large amount of molecules are removed and not recycled, which otherwise would be able to cause AGE-related complications (advanced glycolysation end products). If the increased amount of protein is used to reduce the glucose content in the PD solution, this results also in a reduced exposure to AGE-inducing substances or precursors. In addition, protein has the capability of binding or neutralising the effect of aldehydes and other glucose degradation products.

In accordance with the present invention the patient is isolated from pumps and the like during separation of the protein fraction, which preferably occurs at high pressure in order to reduce the time for the separation. In this way the patient is subject to less risk according to the present invention compared to earlier similar methods. Higher pressure can be used without risk to the patient, which means that a smaller and cheaper filter can be used.

The invention can also be applied to other types of cyclers than that described above. A skilled person understands the modifications which are required.

Figure 7:
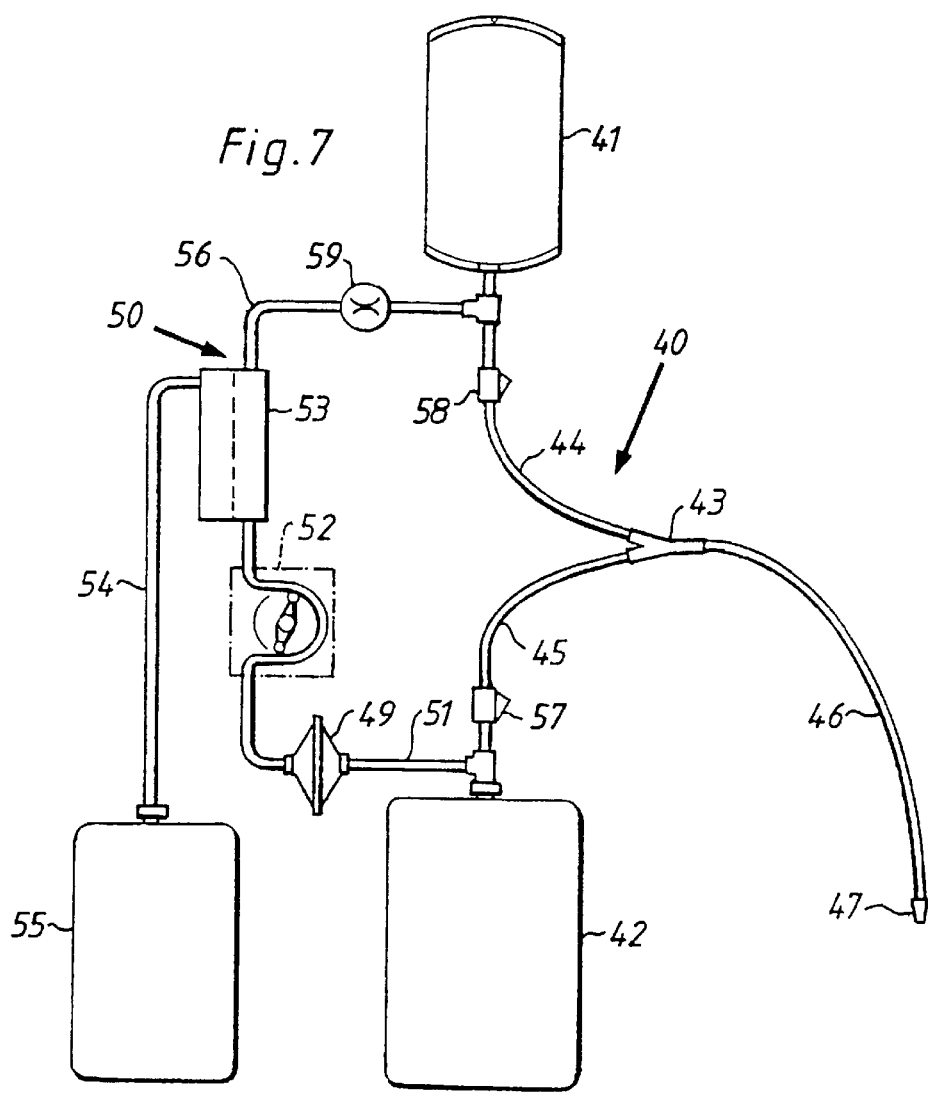
FIG. 7 is a schematic diagram of the principle of a CAPD tube-set equipped with a protein separator in accordance with the present invention.

The invention can also be applied to CAPD by using an addition in the form of a protein separator as shown in FIG. 7.

A conventional tube set 40 for CAPD contains a storage bag 41, a drain bag 42, a Y-coupling 43 and three tubes 44, 45 and 46 which connect the Y-coupling to the storage bag, the drain bag and the patient. The storage bag contains sterile PD solution. The patient is connected to a patient coupling 47 at the end of the patient tube 46. Then the used PD solution is emptied into the storage bag and finally the patient is filled with fresh solution from the storage bag. The various steps are carried out in that the patient moves or manoeuvres the tube clamps and the transport of the liquids occurs by means of the force of gravity.

According to the present invention, a protein separator 50 is used consisting of a first tube 51, a tube pump 52 (a peristaltic pump), a filter 53, a second tube 54, a drain bag 55 and a third tube 56. The first tube 51 is connected to the drain bag 42 either via a T-coupling or by using a needle which passes through a septum. The second tube 56 is connected to the storage bag 41 in the same way. The whole protein separator is arranged at the same level as the drain bag 42, i.e. on the floor. The storage bag 41 is positioned on a stand, normally at a height of about 1.5 m to 2 m above the ground.

The function is the same as described above. After a patient drain to the drain bag 42, the patient activates the tube pump 52, which pumps the contents in the drain bag via the tube 51, the pump 52, the filter 53 and the tube 54 to the waste bag 55. The retentate fraction which cannot pass the filter's membrane passes up via the tube 56 to the storage bag. Due to the hydrostatic pressure the protein fraction is concentrated, so that as little a part as possible of the spent PD solution follows the protein fraction.

After all the liquid has passed from the drain bag 42 to the waste bag 55 the protein separation is ready. The contents in the storage bag is now supplied to the patient.

The patient may shut tube clamps 57, 58 on the tubes 45 and 44 in order to ensure that no pressure conditions, which occur during the protein separation, affect the patient.

It can be suitable to provide the tube 51 with a filter 49 to prevent fibrin and other larger aggregations from reaching the filter or passing up to the storage bag. The same measure can be applied in the tube 18 in the embodiment in FIGS. 1 to 6. The filter can be a filter which is used in a drip chamber in connection with extracorporeal blood treatment.

If the hydrostatic pressure is insufficient to concentrate the protein-rich fraction to a sufficient extent, the tube 56 can be provided with a restriction 59, which contributes to the concentration. The restrictor 59 is dimensioned together with the pump and the filter in order to give the desired concentration. The same measure can be applied in the embodiment of FIGS. 1 to 6 in the tube 24.

Figure 8:
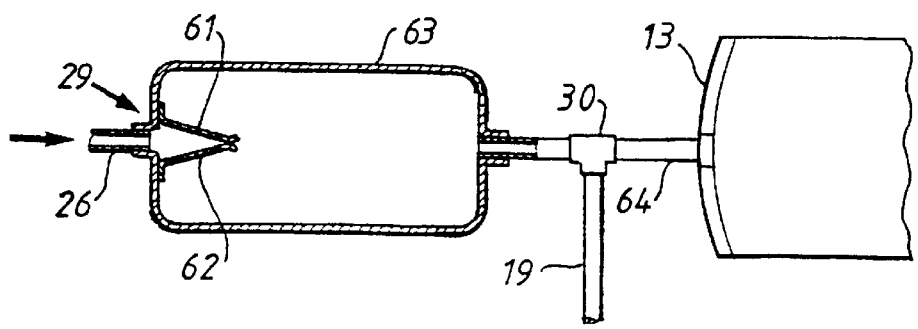
FIG. 8 is a detailed view of a one-way valve included in the tube set.

During the step of protein filling there is a risk that air will enter into the tube 64 between the T-connector 30 and the heater bag (see FIG. 8). It would be unsuitable to feed such air bubbles into the patient.

In accordance with the present invention, the one-way valve 29 is therefore formed as a little bag 63 provided with two plastic sheets which form the one-way valve or butterfly valve as shown in more detail in FIG. 8.

The one-way valve 29 thus comprises two flaps 61 and 62 which open when fluid flows to the right in FIG. 8 but close when fluid flows to the left in FIG. 8. The flaps are positioned in a bag 63 which has a volume of about 20 ml. The bag has a certain stiffness so that it is normally in an expanded condition.

During protein filling, there is first an over-pressure in the heater bag 13, whereby the bag 63 is entirely expanded. During drain of the protein bag to the heater bag 13 the pressure in the pressure chamber is reduced successively to a negative pressure of −67.5 mm Hg. The bag 63 will thus collapse during the last part of the emptying of the protein bag. During the final phase of emptying of the protein bag, a possible amount of air which was in the protein bag can be fed into the heater bag via the tube 26 and the T-coupling 30. The air which enters into the heater bag goes to its upper part and remains there. The air bubbles which remain in the tube 64 between the T-coupling 30 and the heater bag 13 can cause problems.

In accordance with the invention, no fill of the contents of the heater bag to the patient occurs however before the pressure in the pressure chamber has risen to +40 mm Hg. When the pressure rises above atmospheric pressure, the contents in the tube 64 between the heater bag 13 and the bag 63 will be fed to the left in FIG. 8 into the bag 63. The bag 63 has a volume of about 20 ml which means that the whole contents in the tube portion 64 between the heater bag 13 and the bag 63 will be fed into the bag 63 including any possible air bubbles. Due to the effect of this bag 63, all risk of feeding-in air bubbles to the patient is avoided.

The same function can be obtained without a combination with a one-way valve, i.e. the bag 63 can be arranged in the tube 26 without containing a one-way valve and the one-way valve can be positioned upstream of the bag 63.

The one-way valves 28 and 29 can be replaced with electrically controlled valves if such is desired, as similarly the tube clamps 31, 32 and 33.

Above it is defined that the protein is enriched. Protein is intended to mean albumin, immunoglobins, orosomucoid, opsonines and other proteins as well as other substances with a molecular weight which is higher than the permeability characteristic of the filter.

The fraction which passes through the filter is sent to a waste receiver which can imply a tube to a waste receiver in an appartment or that the fraction is collected in a waste receiver bag.

The protein-rich fraction in the protein bag is supplied to the PD solution which is to be fed to the patient. If the fresh PD solution is manufactured on-line by a machine, the contents of the protein bag can be continually metered to the PD solution which is fed into the patient. It may also be possible to first feed in all PD solution to the patient and then add the protein-rich fraction, after which it mixes with the PD solution which is present, in vivo.

The back pressure which is required to obtain a concentrated protein fraction is created according to the above-described embodiments by a hydrostatic pressure. It is to be understood that other alternatives are suitable such as enclosing the protein bag in a container and exposing it to a suitable air pressure. Such a container can be arranged in the PD cycler and obtains pressurised air from the same source as the pressure chamber. The higher the back-pressure, the higher the concentration of the protein fraction. A suitable pressure can be about 100–200 mm Hg. Alternatively, a spring device can produce a back pressure or a weight acting on the bag. Another alternative is a restriction on tube 24.

The protein bag suitably has a maximum volume of about 200–500 ml. The heater bag and the drain bag can suitably have a volume of 2–4 liters. The filter 21 and its membrane 22 should have a high hydraulic permeability so that the back-pressure can be kept low, and a large area such as preferably more than 1 square meter. By using higher pressures and higher back-pressures from the protein bag, for example by including a restriction in tube 24, a simpler filter with a smaller area can be used.

The invention has been described above with reference to preferred embodiments. A skilled person understands that the invention can be combined in other ways than the above-described combinations and such combinations which are obvious for the skilled man are intended to be included in the scope of the invention. The invention is only limited by the appended claims.

What is claimed is:

1. Apparatus for peritoneal dialysis by supplying a fresh peritoneal dialysis solution to a patient comprising a drain bag, a first conduit portion for draining spent peritoneal dialysis solution from said patient to said drain bag, a filter for separating a protein enriched fraction of said spent peritoneal dialysis solution from a protein lean fraction of said spent peritoneal dialysis solution, a second conduit portion for passing said spent peritoneal dialysis solution from said drain bag through said filter, and a third conduit portion for supplying said protein enriched fraction of said spent peritoneal dialysis solution to said fresh peritoneal dialysis solution for supply to said patient.

2. The apparatus of claim 1 including a protein bag, and a fourth conduit portion for collecting said protein enriched fraction of said spent peritoneal dialysis solution in said protein bag for storage prior to said supply of said protein enriched fraction of said spent peritoneal dialysis solution to said fresh peritoneal dialysis solution through said third conduit portion.

3. The apparatus of claim 1 including a waste receiver for receiving said protein lean fraction of said spent peritoneal dialysis solution.

4. The apparatus of claim 1 including restriction means disposed upstream of said protein bag for increasing flow resistance during said collecting of said protein enriched fraction of said spent peritoneal dialysis solution to said protein bag.

5. The apparatus of claim 1 including mounting means for mounting said protein bag at a predetermined height above said filter whereby a predetermined hydraulic pressure is provided therein.

6. A method of peritoneal dialysis by supplying a fresh peritoneal dialysis solution to a patient comprising draining spent peritoneal dialysis solution from said patient to a drain bag, passing said spent peritoneal dialysis solution from said drain bag through a filter so as to separate a protein enriched fraction of said spent peritoneal dialysis solution from a protein lean fraction of said spent peritoneal dialysis solution, and supplying said protein enriched fraction of said spent peritoneal dialysis solution to said fresh peritoneal dialysis solution for supply to said patient.

7. The method of claim 6 including collecting said protein enriched fraction of said spent peritoneal dialysis solution in a protein bag for storage-prior to said supplying of said protein enriched fraction of said spent peritoneal dialysis solution to said fresh peritoneal dialysis solution.

8. The method of claim 7 including increasing the flow resistance during said collecting of said protein enriched fraction of said spent peritoneal dialysis solution to said protein bag.

9. The method of claim 7 including disposing said protein bag at a predetermined height above said filter whereby a predetermined hydraulic pressure is provided therein.

10. The method of claim 6 including transferring said protein lean fraction of said spent peritoneal dialysis solution to a waste receiver.

* * * * *

UNITED STATES PATENT AND TRADEMARK OFFICE
CERTIFICATE OF CORRECTION

PATENT NO. : 6,585,682 B1
DATED : July 1, 2003
INVENTOR(S) : Borje Haraldsson, Jan-Bertil Jeppsson and Bengt-Olov Thell It is certified that error appears in the above-identified patent and that said Letters Patent is hereby corrected as shown below:

Column 12,
Line 41, delete "-".

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,585,682 B1
DATED          : July 1, 2003
INVENTOR(S)    : Börje Haraldsson et al.

It is certified that error appears in the above-identified patent and that said Letters Patent is hereby corrected as shown below:

Delete the entire specification columns 1-12 and substitute therefore the attached specification columns 1-14.

Signed and Sealed this

Fourteenth Day of June, 2005

JON W. DUDAS
*Director of the United States Patent and Trademark Office*

METHOD AND APPARATUS FOR PREVENTING PROTEIN LOSS WITH PERITONEAL DIALYSIS

FIELD OF THE INVENTION

The present invention relates to the field of peritoneal dialysis, so-called PD, and in particular to automatic peritoneal dialysis, so-called APD. A problem with peritoneal dialysis is loss of protein, particularly albumin. More particularly, the present invention relates to a method and an apparatus for preventing protein loss with PD.

BACKGROUND OF THE INVENTION

Peritoneal dialysis means that dialysis occurs by using one of the body's own membranes in the peritoneal cavity; namely, the peritoneal membrane. A PD solution is placed in the peritoneal cavity inside the peritoneal membrane by means of a catheter which passes through the skin and into the peritoneal cavity. Slightly more than two liters of fluid can often be placed in the peritoneal cavity without the patient feeling any great discomfort.

The most common form of PD today is CAPD; namely, continuous ambulatory peritoneal dialysis. With CAPD, a set of bags is used which are coupled to the patient's catheter, in order, with the aid of gravity, to drain the spent PD solution from the patient's peritoneal cavity into a waste bag and to add new PD solution to the patient from a sterile storage bag.

With APD, a machine is used, i.e., a so-called cycler, for achieving the necessary flows into and out of the patient. The machine transports PD solution from storage bags to the cycler, where it is heated, and further to the patient, and transports the PD solution from the patient to the cycler and further to a waste receiver. The cycler is provided with a measurement device which monitors the flows into and out of the patient. APD can be used during the night, and may be more effective than CAPD. With APD, the patient avoids heavy lifting since the PD solutions do not need to be hung up in a high position, which is required with CAPD.

One complication with dialysis is protein loss. The patient often already has a low amount of protein in the blood long before the treatment starts. The dialysis treatment brings about additional losses of protein. A low protein content in a patient is a risk factor which is coupled to high morbidity and mortality with hemodialysis.

In a normal healthy patient, the peritoneal cavity contains about 200 ml of a solution with a composition which is similar to blood plasma. This liquid contains proteins such as albumin and immunoglobins in a predetermined concentration. The concentration of albumin (from 20 to 30 g/l) in the peritoneal cavity is made up of an inward flow from the blood path to the peritoneal cavity, which normally occurs through the peritoneal membrane, and an outflow of albumin through the lymph pathways. The composition of the fluid varies from person to person.

With peritoneal dialysis, the protein content in the fluid inside the peritoneal cavity is diluted and its colloid osmotic pressure is thereby lowered, that pressure, however, being replaced by a high amount of glucose which creates the necessary crystal osmotic gradient in order to remove fluid from the patient.

The fluid which is present in the peritoneal cavity during peritoneal dialysis is thus different than that which is normally present in the peritoneal cavity of healthy persons in at least two respects, namely a high glucose content and a low protein content. There is reason to believe that both characteristics may lead to complications, and it would therefore be desirable to raise the content of protein in order to be able to reduce the glucose content.

It is known that the increased exposure to glucose in a PD patient may lead to hyperinsulinemia, with associated risk of cardio-vascular disease.

Additionally, a daily loss of albumin and other protein substances of about 5 g to 25 g occurs by the spent dialysis solution being led to a waste receiver or to a waste bag which is later discarded.

The abnormally low content of immunoglobulins which are present in the peritoneal cavity during PD probably contributes to an increased risk of peritonitis.

Protein has a buffer capacity, and a reduced content of proteins in the peritoneal cavity means that a PD solution with low pH is neutralized to a lesser extent, or more slowly, during filling of the peritoneal cavity.

With PD it has previously been proposed to circulate the PD solution in a closed circuit, whereby protein losses and losses of other substances are avoided. The PD solution is allowed to pass on one side of a membrane in a dialyser where the PD solution is regenerated by dialysis against an outer dialysis solution whereby waste products are removed. See, for example, U.S. Pat. Nos. 4,338,190; 5,141,493 and 4,276,175.

In International Patent Application No. WO 97/47337, the PD solution is regenerated by means of a semi-permeable membrane in order to raise the osmotic effect of the proteins within the PD solution and to use these proteins as osmotic means. If necessary, other components such as electrolytes or amino acids are added.

These known constructions attack the problem of protein loss. However, these known constructions are difficult to carry out in practice.

They require use of a double-lumen-catheter with simultaneous inlet and outlet to the peritoneal cavity, in order to obtain a continuous flow. It can be difficult to make such a continuous flow be effective, since the PD solution can easily pass more or less straight through between the inlet and the outlet without coming into close contact with the peritoneal membrane.

Another problem is that a circulation pump is required in order to drive the PD solution in the intended circuits. The pump must have the capacity to achieve the required circulation. If any component in the circuit should have a fault, such as a hole in a semi-permeable membrane, there is a risk that the patient will be subjected to much too large a pressure from the pump, being either an under-pressure or an over-pressure.

A third problem is that the aforementioned constructions are often expensive since they require many expensive components, both in the required cycler and for disposable components.

One object of the present invention is to provide a method and an apparatus which prevents protein loss with peritoneal dialysis, particularly with APD.

Another object of the present invention is to provide a method which can be used with a conventional cycler, whereby the cost can be kept low.

Yet another object of the present invention is to provide a method and an apparatus which do not risk subjecting the patient to too high a pressure, even if a fault should occur in the disposable products which are used.

Another object of the present invention is to provide a method and an apparatus which can be used with a normal catheter having only one passage.

Yet another object of the present invention is to provide a method and an apparatus which prevents protein loss and in which dialysis solution is continuously or intermittently supplied from a source of PD solution, and spent PD solution is continuously or intermittently removed from the patient to a waste receiver.

SUMMARY OF THE INVENTION

In accordance with the present invention, these and other objects have now been realized by the invention of a method of peritoneal dialysis by supplying a fresh peritoneal dialysis solution to a patient comprising draining spent peritoneal dialysis solution from the patient to a drain bag, passing the spent peritoneal dialysis solution from the drain bag through a filter so as to separate a protein enriched fraction of the spent peritoneal dialysis solution from a protein lean fraction of the spent peritoneal dialysis solution, and supplying the protein enriched fraction of the spent peritoneal dialysis solution to the fresh peritoneal dialysis solution for supply to the patient. In a preferred embodiment, the method includes collecting the protein enriched fraction of the spent peritoneal dialysis solution in a protein bag for storage prior to the supplying of the protein enriched fraction of the spent peritoneal dialysis solution to the fresh peritoneal dialysis solution.

In accordance with one embodiment of the method of the present invention, the method includes transferring the protein lean fraction of the spent peritoneal dialysis solution to a waste receiver.

In accordance with another embodiment of the method of the present invention, the method includes increasing the flow resistance during the collecting of the protein enriched fraction of the spent peritoneal dialysis solution to the protein bag.

In accordance with another embodiment of the method of the present invention, the method includes disposing the protein bag at a predetermined height above the filter whereby a predetermined hydraulic pressure is provided therein.

In accordance with the present invention, these and other objects have also been realized by the invention of apparatus for peritoneal dialysis by supplying a fresh peritoneal dialysis solution to a patient comprising a drain bag, a first conduit portion for draining spent peritoneal dialysis solution from the patient to the drain bag, a filter for separating a protein enriched fraction of the spent peritoneal dialysis solution from a protein lean fraction of the spent peritoneal dialysis solution, a second conduit portion for passing the spent peritoneal dialysis solution from the drain bag through the filter, and a third conduit portion for supplying the protein enriched fraction of the spent peritoneal dialysis solution to the fresh peritoneal dialysis solution for supply to the patient. Preferably, the apparatus includes a protein bag, and a fourth conduit portion for collecting the protein enriched fraction of the spent peritoneal dialysis solution in the protein bag for storage prior to the supply of the protein enriched fraction of the spent peritoneal dialysis solution to the fresh peritoneal dialysis solution through the third conduit portion.

In accordance with one embodiment of the apparatus of the present invention, the apparatus includes a waste receiver for receiving the protein lean fraction of the spent peritoneal dialysis solution.

In accordance with another embodiment of the apparatus of the present invention, the apparatus includes restriction means disposed upstream of the protein bag for increasing flow resistance during the collecting of the protein enriched fraction of the spent peritoneal dialysis solution to the protein bag.

In accordance with another embodiment of the apparatus of the present invention, the apparatus includes mounting means for mounting the protein bag at a predetermined height above the filter whereby a predetermined hydraulic pressure is provided therein.

In order to meet these objects, a method is provided according to the present invention for preventing protein loss with peritoneal dialysis, comprising draining spent PD solution from a patient to a drain bag, passing the spent PD solution in the drain bag through a filter device for enrichment of a protein-rich fraction, and supplying the protein-rich fraction to a fresh PD solution intended to be supplied to the patient.

The protein-rich fraction or filter retentate is suitably collected in a protein bag for later supply to the fresh PD solution, while the protein-lean fraction or filtrate passing through the filter is sent to a waste receiver.

The protein bag may be positioned at a predetermined height above the filter in order to achieve a hydraulic back-pressure.

The present invention also relates to an apparatus for carrying out the aforementioned method. The apparatus includes a device for draining spent PD solution from a patient to a drain bag, a device for passing spent PD solution in the drain bag through a filter device for enrichment of a protein-rich fraction, and a device for supplying the protein-rich fraction to a fresh PD solution intended to be supplied to the patient.

The apparatus also suitably comprises a device for collecting the protein-rich fraction in a protein bag for later supply to the fresh PD solution, and a device for sending the protein-lean fraction passing through the filter to a waste receiver.

BRIEF DESCRIPTION OF THE DRAWINGS

Figure 9:
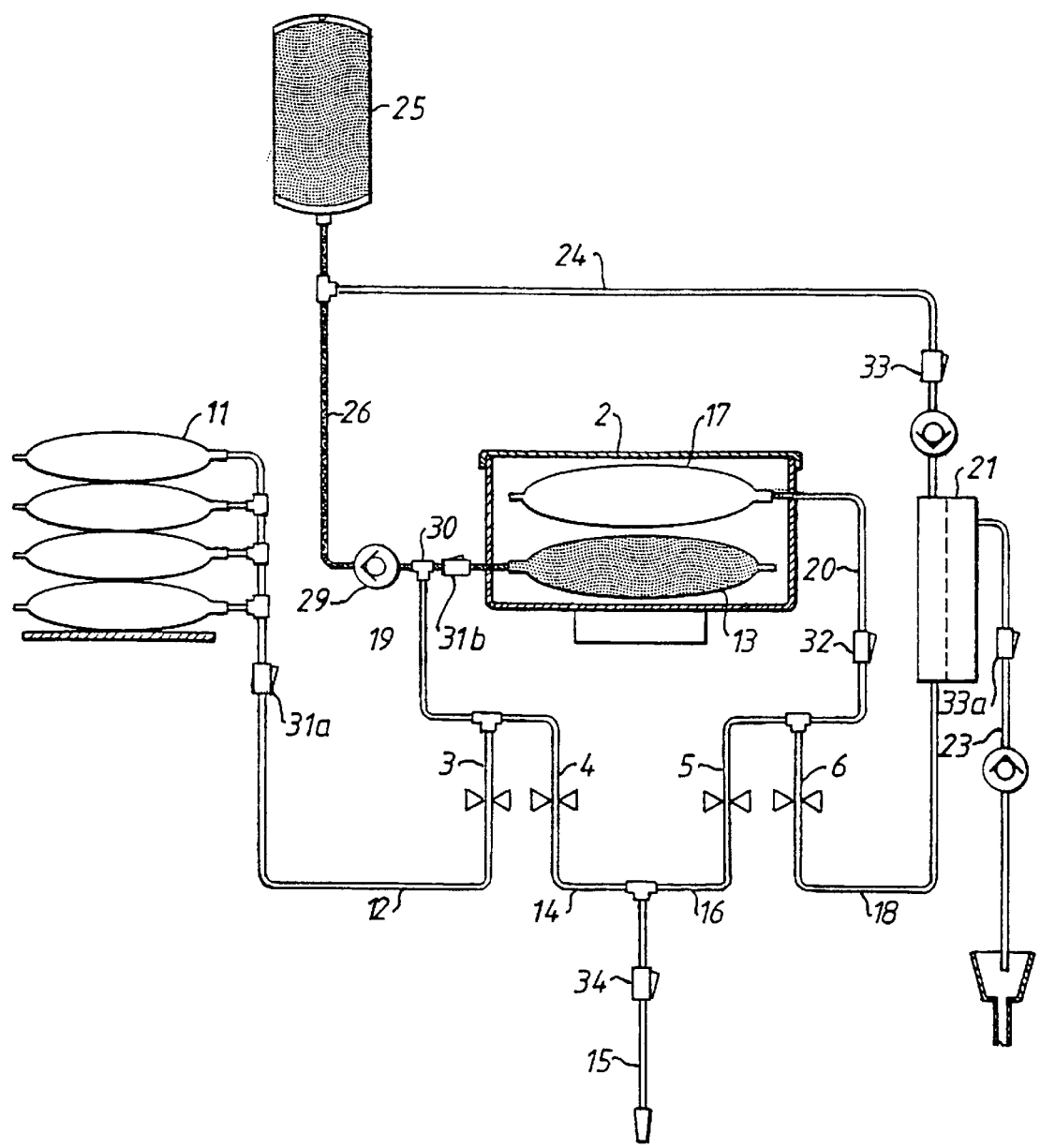
FIG. 9 is a schematic diagram similar to FIG. 5, of a slightly modified cycler tube set.

Additional objects, advantages and features of the present invention are disclosed in more detail in the following detailed description of several embodiments of the present invention with reference to the drawings, in which:

FIG. 1 is a front, elevational, schematic representation of the principle of a cycler provided with a tube-set intended for APD with which the present invention can be used, in an initial position;

FIG. 2 is a front, elevational, schematic representation of the principle of the cycler shown in FIG. 1 in a first position, called HF;

FIG. 3 is a front, elevational schematic representation of the principle of the cycler shown in FIG. 1 in a second position, called PD;

FIG. 4 is a front, elevational schematic representation of the principle of the cycler shown in FIG. 1 in a third position, called SD;

FIG. 5 is a front, elevational schematic representation of the principle of the cycler shown in FIG. 1 in a fourth position, called PrF;

FIG. 6 is a front, elevational schematic representation of the principle of the cycler shown in FIG. 1 in a fifth position, called PF;

FIG. 7 is a front, elevational schematic representation of the principle of a CAPD tube-set equipped with a protein separator in accordance with the present invention;

FIG. 8 is a side, elevational, partially sectional detailed view of a one-way valve included in the tube set; and FIG. 9 is a front, elevational, schematic representation of a slightly modified cycler tube set as compared to that shown in FIG. 5.

DETAILED DESCRIPTION

Referring to the drawings, FIG. 1 discloses an overview of a cycler and a tube-set intended for APD and during use of the method of the present invention.

The cycler is shown schematically, and only consisting of a pressure chamber 2 and four valve clamps, 3, 4, 5, and 6. The cycler is of a construction which is disclosed in International Application No. WO 95/20985, the disclosure of which is incorporated herein by reference thereto.

The cycler is provided with a tube-set 10 consisting of several bags joined together with tubes. The tube-set can be manufactured of PVC and is sterilized. More closely defined, the tube-set includes storage bags 11 for fresh PD solution, FIG. 1 showing four bags coupled in parallel. The storage bags 11 are joined by first tube 12 to a heater bag 13. The heater bag 13 is furthermore joined with a patient by means of a second tube 14 and a patient connector tube 15. The patient connector tube 15 is joined by means of a third tube 16 to a drain bag 17 which, in turn, is joined to a waste receiver by means of a fourth tube 18.

The heater bag 13 and the drain bag 17 are positioned in the pressure chamber 2. The tubes, 12, 14, 16, and 18, pass through valve clamps as shown in FIG. 1. The tubes, 12 and 14, unite into a common tube 19 beyond the valve clamps, which tube 19 leads by means of a through-way bushing into the pressure chamber to the heater bag 13. In a similar way, the tubes, 16 and 18, unite beyond the valve clamps, 5 and 6, into a common tube 20 which leads by means of a through-way bushing into the pressure chamber to the drain bag 17.

As is clear from International Application No. WO 95/20985, the pressure chamber 2 can be subjected to an under-pressure or an over-pressure. The pressure chamber can, together with the valve clamps, 3, 4, 5 and 6, control the flow of fresh PD solution from the storage bags to the heater bag, and from there to the patient, and spent PD solution from the patient to the drain bag and further to the waste receiver. The flow is monitored in that the pressure chamber is weighed on electronic scales, whereby the flow of PD solution into and out of the heater bag and drain bag, respectively, can be detected and controlled.

Different PD operation cycles are possible, which is understood by a skilled man and which is described in more detail in International Application No. WO 95/20985.

In order to prevent protein loss in accordance with the present invention, the previously known tube set is somewhat modified. Thus, a filter 21 with a semipermeable membrane 22 is added to the tube 18 which leads to the waste receiver. The semipermeable membrane has a structure and dimensions such that it holds or prevents passage of molecules and particles larger than a minimum diameter, which is normally defined in terms of molecular weight for the molecules which cannot pass through the membrane. In the present case, the semipermeable membrane has the capacity to hold molecules larger than about 20,000 to 50,000 Daltons. The membrane is constructed so as to safely prevent passage of albumin which has a molecular size of 68,000 Daltons. The protein-lean fraction which passes through the membrane is led by means of a fifth tube 23 to the waste receiver.

The protein-rich fraction which cannot pass through the membrane is led by means of a sixth tube 24 to a protein bag 25. A seventh tube 26 leads from the protein bag 25 to a T-coupling 30 on the tube 19, which leads to the heater bag 13.

Additionally, the tube set is provided with three one-way valves, 27, 28 and 29, in tubes, 23, 24 and 26, respectively, as shown in FIG. 1. Furthermore, there are three tube clamps, 31, 32 and 33, arranged on the tubes, 19, 20 and 24, respectively, as shown in FIG. 1.

The function of the present invention will be disclosed in the following description by the various steps in the method according to the present invention with reference to FIGS. 2–6.

Before the present invention can be applied, the filter needs to be "primed", i.e. filled with fluid so that all the air within the filter is displaced. This occurs in a first priming step which is described with reference to FIG. 1. Firstly the clamps, 31, 32 and 33, are closed as well as a clamp 34 located on the patient tube. The filter 22 is adjusted such that the end positioned closest to the connection 37 to the tube 23 is highest. The valves, 3, 4, 5 and 6, are opened, which may occur manually or in another suitable way. One of the storage bags 11 is raised up somewhat so that it is located above the level of the filter, whereby the PD solution flows through the tube 12, the valve 3 and the valve 4 to the tube 14 as well as further through the tube 16 and the valves 5 and 6 to the tube 18 where the PD solution reaches the lower connection 36 of the filter. In this way the PD solution forces the air which is in the filter out through the connection 37 and through the tube 23 to the waste receiver. Since the clamps, 31, 34, 32 and 33, are closed, no solution will flow into the heater bag 13, the patient connection tube 15, the drain bag 17 or the tube 24. When the filter is completely filled with PD solution, and there are no more air bubbles in the tube 23, the tubes clamp 34 is opened so that the patient connection 15 is also filled with PD solution up to the patient connector 38, whereupon the clamp 34 is closed again.

It is understood that as an alternative to using PD solution for priming purposes, a separate bag with priming solution, such as a sterile physiological common salt solution, can be connected to a coupling on the tube 12.

Parts of the tube set and the filter are now filled with PD solution. Then the tube clamps 31, 32 and 33 are removed and the cycler is ready for use.

As is clear from FIG. 2, the cycler proceeds by filling the heater bag with PD solution from the storage bags 11 (Heater Fill, HF) by the valve 3 being opened when the pressure chamber has an under-pressure (e.g., −100 mm Hg). The other valves are closed. The contents in the heater bag is heated to about 37° C. The amount of PD solution which is fed into the heater bag is determined by the user by entering a patient fill volume into the cycler's computer 39, and is regulated with the aid of the cycler's scales.

During this time, the patient connects himself to the patient coupling 38 using aseptic technology in a conventional way. Thereafter, the clamp 34 is opened or removed. The tubes 14 and 16 are suitably united into a double tube so that the tube 15 is as short as possible, which minimizes the dead space (see European Application No. 499,718).

Thereafter, the patient is emptied of spent PD solution (Patient Drain, PD) which occurs by the pressure chamber being exposed to an under-pressure of about −65 mm Hg and the valve 5 is opened while the other valves are shut. The spent PD solution flows from the patient through the tubes, 15, 16 and 20, to the drain bag 17. When the drain step is complete, the valve 5 is shut, which is determined by the flow to the drain bag having stopped or having been reduced in a predetermined way.

Then, the cycler carries out steps which are particularly related to the present invention. This occurs during a system drain step (System Drain, SD) shown in FIG. 4, where the contents in the drain bag is fed out to the waste receiver. The pressure chamber is exposed to an over-pressure of about +100 mm Hg, and the valve 6 is opened while the other valves are closed. In this way the contents in the drain bag 17 is fed out through the tubes, 20 and 18, to the inlet connector 36 of the filter.

The protein bag 25 is arranged on a stand at a predetermined height above the cycler 1 and the filter 21. The PD solution which enters the filter by means of the connector 36 first passes straight through the filter and out through the outlet 35 to the tube 24 until the hydrostatic pressure causes a part of the fluid in the PD solution to be passed through the filter and out to the outlet by means of the tube 23. The retentate fraction which is held by the filter is thereby enriched in protein and other substances having a molecular weight over about 50,000 Daltons. The enriched fraction on the inlet side of the membrane applies a colloid osmotic pressure across the membrane. When the mentioned osmotic pressure is equal to the hydrostatic back-pressure in the tube 24, the retentate fraction cannot be further enriched and is passed to the protein bag 25.

By adjusting the height of the protein bag and depending upon the characteristics of the filter, a part of the contents in the drain bag will be filtered and pass out to the waste receiver by means of the tube 23, the filtrate, and a part will pass to the protein bag, the retentate. The volume ratio between the protein-rich fraction and the protein-lean fraction can be about 5% to 25% depending on the height of the protein bag and the amount of protein in the contents of the drain bag. The higher the protein content in the drain bag, the higher its osmotic effect and the lower the proportion of the volume passing to the waste receiver.

In accordance with the present invention it is sought to concentrate the protein-rich fraction as much as possible without the fraction becoming too viscous or having too high an osmotic pressure arising across the membrane. A degree of concentration of 4 to 20 is sought.

When the drain bag is emptied and all the spent PD solution has either been fed out to the waste receiver through the filter or has been moved to the protein bag, this step is finished which is controlled with the aid of the scales in the cycler.

Then, all the valves 3–6 are closed while the pressure in the pressure chamber drops from +100 mm Hg to −65 mm Hg. Then, the contents in the protein bag can flow through the tube 26 to the heater bag in a protein filling step (Protein Fill, PrF). The one-way valve 28 ensures that the protein fraction does not flow back to the filter 21. The heater bag 13 is already filled with PD solution so the protein fraction is diluted to about the same or slightly lower concentration as it originally had in the drain bag.

By transfer of the protein fraction, the contents of the heater bag will increase, but the increase is very slight, and is tolerated in most cases by the patient. In other cases the fill volume may be slightly reduced. The increase in the volume is monitored by the machine by means of its scales.

Lastly, a patient fill (Patient Fill, PF) occurs by the pressure chamber being exposed to an over-pressure of about +80 mm Hg and the valve 4 is opened while the other valves are shut.

After this, the sequence is resumed by a filling of the heater bag (HF).

By using the filter 21 and the protein bag 25 the proteins which are in the used PD solution will be utilized and fed back to the patient by means of the contents in the heater bag. The protein fraction in the drain bag is concentrated as much as possible before it is transferred to the heater bag, since the fluid which follows with the protein fraction becomes ineffective with respect to the dialysis treatment since it has already been used once.

In this way, the protein content in the patient's peritoneal cavity will adjust itself to a value where the inflow by means of the peritoneal membrane balances the outflow by means of the lymph pathways, as in a healthy patient, but the volume of fluid in the peritoneal cavity is about 10 times larger. In this way the osmotic effect of the proteins will be utilized, which can be used to reduce the concentration of glucose in the PD solution.

Reduced glucose load is expected to give reduced hyperinsulinemia, which reduces the risk for arteriosclerosis and thereby reduces complications in the form of cardiovascular complications.

It can be expected that the higher protein content in the PD solution will have a beneficial effect on the peritoneal membrane so that its characteristics vary less during the dialysis treatment. Additionally, the increased concentration of immunoglobulins may result in a reduced occurrence of peritonitis.

The supply of the protein fraction to the contents in the heater bag effects neutralization of its contents, so that it obtains a physiological pH of from about 7.2 to 7.4. In this way, exposure of the peritoneal cavity to a solution with too low a pH is avoided, which exposure is understood to cause pain during the fill phase, and which may result in damage to the peritoneal membrane, as well as the cells which are in the peritoneal cavity.

Additionally, the proteins absorb the glucose degradation products which are in the contents of the heater bag, so that these products are not able to act on the proteins and other amino compositions which are present in the peritoneal cavity. These glucose degradation products are presumed to be AGE precursors. Thus, the exposure of the patient to AGE-inducing substances is decreased.

The extra steps which are required according to the present invention increase the time from the patient drain (PD) to the patient fill (PF), thereby reducing the effective dialysis time. Without using the present invention, a patient drain should be able to be followed directly by a patient fill without an intermediate system drain and protein bag filling. The time span between these two steps may be about 10 minutes. However, the beneficial effects of the present invention should outweigh this disadvantage.

It is possible to carry out separation of the contents of the drain bag after the patient fill, i.e. the step in FIG. 6 is placed between the steps according to FIGS. 3 and 4. In this way, no dialysis treatment time is lost. The protein bag will then contain the protein-rich fraction between the patient fills and feed this directly into the heater bag before the patient fill. However, the first patient fill will occur with a heater bag content which is not enriched with proteins. The next patient fill, however, will occur with an acceptably high protein concentration.

The last patient fill during the night should, however, occur in the first described manner, so that the PD solution fed out from the patient is first separated for protein and this protein fraction is supplied to the patient in addition to the fraction which has already been supplied, i.e. a full dose of protein is supplied to the patient. In this way, the proteins are always stored in the patient's peritoneal cavity between dialysis treatments, such as during the daytime for a patient being treated with APD during nighttime.

Alternatively, the last protein dose can also be stored in the protein bag during the day, and at the start of the next treatment this protein dose can also be used to protein-enrich the first patient fill. This requires, however, that the protein fraction is not damaged by being stored during the day up to the connection of the patient the next evening, and that bacteria have no possibility to grow.

Normally, the heater bag includes from about 10% to 15% extra PD fluid, which is not supplied to the patient, because of the risk of entering air into the patient. Such air is always present in the system and is separated from the fluid in the heater bag during the heating step and accumulates in the heater bag. By infusing less than the complete contents of the heater bag, such air remains in the top of the heater bag. The remaining 10% in the heater bag is discarded after a completed peritoneal dialysis session, such as a night APD treatment. However, this also means that 10% of the albumin present in the last fill to the patient is wasted. Since the concentration is relatively high, such as 20 g/l, this means that up to about 4 to 6 grams of albumin are wasted for a two liter fill volume.

According to the present invention, this waste of albumin may be avoided by making a separate and distinct last fill step. Normally, the last fill is generally different, since the patient in the last fill is prepared for the day time dwell, which may be with a different composition or concentration of glucose, or with a glucose polymer instead of glucose.

Instead of entering the contents of the protein bag into the heater bag, the contents of the protein bag are delivered directly to the peritoneal cavity in advance of the last fill. In order to perform this operation, the tube set shown in FIG. 5 is sligtly modified by moving clamp 31 in FIG. 5 to a position between T-connection 30 and heater bag 13, in the position shown in FIG. 9 by reference numeral 31b. Another clamp 31a is inserted in tube 12 and another clamp 33a is inserted in tube 23.

Instead of entering the contents of the protein bag 25 into the heater bag in the last fill, claim 31b is closed while valve clamp 4 is opened. Due to the gravity forces, the contents of the protein bag flow down the tubes, 26, 19, 14 and 15, into the patient's peritoneal cavity, which at this time is essentially empty. When all of the contents of the protein bag have been filled into the patient, clamp 31b is opened and the contents of the heater bag are filled to the patient. In this manner, only about 1% (about 0.4 grams per day) of the protein is wasted, namely the protein remaining in the heater bag after the second to last fill, and diluted by about two liters of fresh PD solution, of which about 90% is filled to the patient in the last fill.

There is also a waste of protein because some protein is left in the filter and the tube 24. In order to also save these proteins, a separate scavenging step is performed, either before or immediately after the above-mentioned direct protein fill step. Clamp 31a in tube 12 and clamp 33a in tube 23 are closed. Moreover, clamp 34 in tube 15 and clamp 32 in tube 20 are closed. Clamp 31b in tube 19 as well as all valve clamps, 3, 4, 5 and 6, are opened. The pressure chamber is exposed to an over-pressure, whereby the fluid in the heater bag passes through tube 19, tube 14, tube 16 and tube 18 to the filter 21. Because clamp 33a in tube 23 is closed, the fluid passes up through tube 24, clamp 33 being opened, to protein bag 25, thereby bringing all proteins stuck in the retentate side of filter 21 and tube 24 to the protein bag. When about two deciliters have passed through this path, as measured by the scales of the cycler, the scavening step is finished by closing all valve clamps, 3, 4, 5 and 6, and opening clamp 34. Finally, the contents of the protein bag is entered into the peritoneal cavity of the patient. If the scavenging step is performed before the protein patient fill step, the proteins saved by the scavenging step are introduced into the patient together with the other proteins. Otherwise, valve 4 is opened with clamp 31b closed and clamp 34 opened, and the contents of the protein bag enters into the peritoneal cavity of the patient. Finally, the contents of the heater bag is supplied to the patient, as explained above. These three steps may be performed in any desired order.

The method of direct fill of the protein bag to the patient may be performed automatically by using automatically controlled valve clamps in the circuit instead of the manually operated clamps. The method of direct fill of the protein bag to the patient may also be used in more than the last fill, such as also in the second to last fill, etc.

The method according to the present invention is beneficial relative to other previously suggested methods for regeneration of the PD solution, since the spent PD solution is filtered, not dialysed. Such molecules as beta-2-microglobulin which are presumed to cause complications, pass through the filter and to the waste receiver. Also, other so-called "middle molecules" pass through the filter since these follow with the ultrafiltration flow. In previously known methods, dialysis is used to regenerate the PD solution, and it is known that dialysis is not equally as effective as filtration in eliminating these "middle molecules".

By means of the present invention, a large amount of molecules are removed and not recycled, which otherwise would be able to cause AGE-related complications (advanced glycolysation end products). If the increased amount of protein is used to reduce the glucose content in the PD solution, this also results in a reduced exposure to AGE-inducing substances or precursors. In addition, protein has the capability of binding or neutralising the effect of aldehydes and other glucose degradation products.

In accordance with the present invention the patient is isolated from pumps and the like during separation of the protein fraction, which preferably occurs at high pressure in order to reduce the time for the separation. In this way the patient is subject to less risk according to the present invention compared to earlier similar methods. Higher pressure can be used without risk to the patient, which means that a smaller and cheaper filter can be used.

The present invention can also be applied to other types of cyclers than that described above. A skilled person will understand the modifications which are required.

The present invention can also be applied to CAPD by using an addition in the form of a protein separator as shown in FIG. 7.

A conventional tube set 40 for CAPD contains a storage bag 41, a drain bag 42, a Y-coupling 43 and three tubes 44, 45 and 46 which connect the Y-coupling to the storage bag, the drain bag and the patient. The storage bag contains sterile PD solution. The patient is connected to a patient coupling 47 at the end of the patient tube 46. The used PD solution is then emptied into the storage bag, and finally the patient is filled with fresh solution from the storage bag. The various steps are carried out by the patient moving or maneuvering the tube clamps, and the transport of the liquids occurs by means of the force of gravity.

According to the present invention, a protein separator 50 is used consisting of a first tube 51, a tube pump 52 (a peristaltic pump), a filter 53, a second tube 54, a drain bag 55 and a third tube 56. The first tube 51 is connected to the drain bag 42 either by means of a T-coupling or by using a needle which passes through a septum. The second tube 56 is connected to the storage bag 41 in the same way. The whole protein separator is arranged at the same level as the drain bag 42, i.e. on the floor. The storage bag 41 is positioned on a stand, normally at a height of about 1.5 m to 2 m above the ground.

The function is the same as described above. After a patient drain to the drain bag 42, the patient activates the tube pump 52, which pumps the contents in the drain bag through the tube 51, the pump 52, the filter 53 and the tube 54 to the waste bag 55. The retentate fraction which cannot pass the filter's membrane passes up through the tube 56 to the storage bag. Due to the hydrostatic pressure the protein fraction is concentrated, so that as little a part as possible of the spent PD solution follows the protein fraction. After all of the liquid has passed from the drain bag 42 to the waste bag 55 the protein separation is ready. The contents of the storage bag are now supplied to the patient.

The patient may shut tube clamps, 57 and 58, on the tubes, 45 and 44, in order to ensure that no pressure conditions, which occur during the protein separation, affect the patient.

It can be suitable to provide the tube 51 with a filter 49 to prevent fibrin and other larger aggregations from reaching the filter or passing up to the storage bag. The same measure can be applied in the tube 18 in the embodiment in FIGS. 1 to 6. The filter can be a filter which is used in a drip chamber in connection with extracorporeal blood treatment.

If the hydrostatic pressure is insufficient to concentrate the protein-rich fraction to a sufficient extent, the tube 56 can be provided with a restriction 59, which contributes to the concentration. The restrictor 59 is dimensioned together with the pump and the filter in order to provide the desired concentration. The same measure can be applied in the embodiment of FIGS. 1 to 6 in tube 24. During the step of protein filling there is a risk that air will enter into the tube 64 between the T-connector 30 and the heater bag (see FIG. 8). It would be unsuitable to feed such air bubbles into the patient.

In accordance with the present invention, the one-way valve 29 is therefore formed as a little bag 63 provided with two plastic sheets which form the one-way valve or butterfly valve as shown in more detail in FIG. 8.

The one-way valve 29 thus comprises two flaps 61 and 62 which open when fluid flows to the right in FIG. 8 but close when fluid flows to the left in FIG. 8. The flaps are positioned in a bag 63 which has a volume of about 20 ml. The bag has a certain stiffness so that it is normally in an expanded condition.

During protein filling, there is first an over-pressure in the heater bag 13, whereby the bag 63 is entirely expanded. During draining of the protein bag to the heater bag 13 the pressure in the pressure chamber is reduced successively to a negative pressure of −67.5 mm Hg. The bag 63 will thus collapse during the last part of the emptying of the protein bag. During the final phase of emptying of the protein bag, a possible amount of air which was in the protein bag can be fed into the heater bag through the tube 26 and the T-coupling 30. The air which enters into the heater bag goes to its upper part and remains there. The air bubbles which remain in the tube 64 between the T-coupling 30 and the heater bag 13 can cause problems.

In accordance with the present invention, no supply of the contents of the heater bag to the patient occurs, however, before the pressure in the pressure chamber has risen to +40 mm Hg. When the pressure rises above atmospheric pressure, the contents in the tube 64 between the heater bag 13 and the bag 63 will be fed to the left in FIG. 8 into the bag 63. The bag 63 has a volume of about 20 ml, which means that the whole contents in the tube portion 64 between the heater bag 13 and the bag 63 will be fed into the bag 63, including any possible air bubbles. Due to the effect of this bag 63, all risk of feeding air bubbles to the patient is avoided.

The same function can be obtained without a combination with a one-way valve, i.e. the bag 63 can be arranged in the tube 26 without containing a one-way valve and the one-way valve can be positioned upstream of the bag 63.

The one-way valves 28 and 29 can be replaced with electrically controlled valves if such is desired, as similarly the tube clamps, 31, 32 and 33.

It is stated above that the protein is enriched. Protein is intended to mean albumin, immunoglobins, orosomucoid, opsonines and other proteins, as well as other substances with a molecular weight which is higher than the permeability characteristic of the filter.

The fraction which passes through the filter is sent to a waste receiver which can imply a tube to a waste receiver in a compartment, or that the fraction is collected in a waste receiver bag.

The protein-rich fraction in the protein bag is supplied to the PD solution, which is to be fed to the patient. If the fresh PD solution is manufactured on-line by a machine, the contents of the protein bag can be continually metered to the PD solution which is fed into the patient. It may also be possible to first feed in all PD solution to the patient and then add the protein-rich fraction, after which it mixes with the PD solution which is present, in vivo.

The back pressure which is required to obtain a concentrated protein fraction is created according to the above-described embodiments by a hydrostatic pressure. It is to be understood that other alternatives are suitable, such as enclosing the protein bag in a container and exposing it to a suitable air pressure. Such a container can be arranged in the PD cycler and obtains pressurized air from the same source as the pressure chamber. The higher the back-pressure, the higher the concentration of the protein fraction. A suitable pressure can be from about 100 to 200 mm Hg. Alternatively, a spring device can produce a back pressure or a weight acting on the bag. Another alternative is a restriction on tube 24.

The protein bag suitably has a maximum volume of from about 200 to 500 ml. The heater bag and the drain bag can suitably have a volume of about 2 to 4 liters. The filter 21 and its membrane 22 should have a high hydraulic permeability so that the back-pressure can be kept low, and a large area such as preferably more than 1 square meter. By using higher pressures and higher back-pressures from the protein bag, for example by including a restriction in tube 24, a simpler filter with a smaller area can be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for peritoneal dialysis by supplying a fresh peritoneal dialysis solution to a patient comprising a drain bag, a first conduit portion for draining spent peritoneal dialysis solution from said patient to said drain bag, a filter for separating a protein enriched fraction of said spent peritoneal dialysis solution from a protein lean fraction of said spent peritoneal dialysis solution, a second conduit portion for passing said spent peritoneal dialysis solution from said drain bag through said filter, and a third conduit portion for supplying said protein enriched fraction of said spent peritoneal dialysis solution to said fresh peritoneal dialysis solution for supply to said patient.

2. The apparatus of claim 1 including a protein bag, and a fourth conduit portion for collecting said protein enriched fraction of said spent peritoneal dialysis solution in said protein bag for storage prior to said supply of said protein enriched fraction of said spent peritoneal dialysis solution to said fresh peritoneal dialysis solution through said third conduit portion.

3. The apparatus of claim 1 including a waste receiver for receiving said protein lean fraction of said spent peritoneal dialysis solution.

4. The apparatus of claim 1 including restriction means disposed upstream of said protein bag for increasing flow resistance during said collecting of said protein enriched fraction of said spent peritoneal dialysis solution to said protein bag.

5. The apparatus of claim 1 including mounting means for mounting said protein bag at a predetermined height above said filter whereby a predetermined hydraulic pressure is provided therein.

6. A method of peritoneal dialysis by supplying a fresh peritoneal dialysis solution to a patient comprising draining spent peritoneal dialysis solution from said patient to a drain bag, passing said spent peritoneal dialysis solution from said drain bag through a filter so as to separate a protein enriched fraction of said spent peritoneal dialysis solution from a protein lean fraction of said spent peritoneal dialysis solution, and supplying said protein enriched fraction of said spent peritoneal dialysis solution to said fresh peritoneal dialysis solution for supply to said patient.

7. The method of claim 6 including collecting said protein enriched fraction of said spent peritoneal dialysis solution in a protein bag for storage prior to said supplying of said protein enriched fraction of said spent peritoneal dialysis solution to said fresh peritoneal dialysis solution.

8. The method of claim 7 including increasing the flow resistance during said collecting of said protein enriched fraction of said spent peritoneal dialysis solution to said protein bag.

9. The method of claim 7 including disposing said protein bag at a predetermined height above said filter whereby a predetermined hydraulic pressure is provided therein.

10. The method of claim 6 including transferring said protein lean fraction of said spent peritoneal dialysis solution to a waste receiver.

* * * * *